United States Patent [19]

Vandekerckhove

[11] Patent Number: 4,839,231
[45] Date of Patent: Jun. 13, 1989

[54] AGENTS AND PROCEDURES FOR THE TRANSFER OF PROTEINS AND/OR NUCLEIC ACIDS ONTO A SUPPORTED RECEPTOR SURFACE

[75] Inventor: Joel S. Vandekerckhove, Loppem, Belgium

[73] Assignee: Plant Genetic Systems N.V., Brussels, Belgium

[21] Appl. No.: 92,242

[22] Filed: Sep. 2, 1987

Related U.S. Application Data

[63] Continuation-in-part of Ser. No. 866,250, May 23, 1986.

[30] Foreign Application Priority Data

| Jan. 10, 1985 | [FR] | France | 85 14579 |
| Feb. 9, 1985 | [FR] | France | 85 13046 |
| Sep. 2, 1986 | [EP] | European Pat. Off. | 86401933.6 |

[51] Int. Cl.$^4$ ............... B32B 17/10; B32B 27/08; G01N 33/552; C07K 17/00
[52] U.S. Cl. ............... 428/441; 428/333; 428/515; 428/307.3; 428/311.1; 436/86; 525/54.1
[58] Field of Search ............... 428/441, 515, 307.3, 428/311.1, 333, 336, 339; 525/54.1; 436/86, 531, 807

[56] References Cited

U.S. PATENT DOCUMENTS

| 3,927,242 | 12/1975 | Rembaum et al. | 428/341 X |
| 4,006,059 | 2/1977 | Butler | 530/811 X |
| 4,210,722 | 7/1980 | Silver | 530/815 X |
| 4,357,142 | 11/1982 | Schall, Jr. et al. | 530/817 X |
| 4,363,634 | 12/1982 | Schall, Jr. | |
| 4,603,114 | 7/1986 | Hood et al. | 436/89 |
| 4,610,847 | 9/1986 | Hood et al. | 422/231 X |

FOREIGN PATENT DOCUMENTS

| 0102661 | 3/1984 | European Pat. Off. | |
| 81/02790 | 10/1981 | PCT Int'l Appl. | 436/56 |
| WO81/02790 | 10/1981 | PCT Int'l Appl. | |
| WO84/03055 | 8/1984 | PCT Int'l Appl. | |

OTHER PUBLICATIONS

"A Gas-Liquid Solid Phase Peptide and Protein Sequenator", R. M. Hewick et al., J. of Biol. Chem., vol. 256, No. 15, 1981, pp. 7990-7997.

"Protein Blotting & Principles and Applications", Gershoni et al., Anal. Biochem, 131, 1-15 (1983).
Chemical Abstracts, vol. 97, 1982, p. 360; Electrophoretic Transfer of Proteins from Sodium Dodecyl Sulfate-Polyacrylamide Gels to a Positively Charged Membrane Filter.
Chemical Abstracts, vol. 88, 1978, p. 206; Polyquaternary Amines Prevent Peptide Loss from Sequenators.
Aebersold et al; The Journal of Biological Chemistry; vol. 261, No. 9; Mar. 25, 1986; pp. 4229-4238; Electroblotting onto Activated Glass.
Renart et al.; Proc. Natl. Acad. Sci., U.S.A.; vol. 76, No. 7; pp. 3116-3120; Jul., 1987; Transfer of Proteins from Gels to Diazobenzyloxymethyl-Paper and Detection with Antisera; A Method for Studying Antibody Specificity and Antigen Structure.
Proc. Natl. Acad. Sci., U.S.A.; vol. 76, No. 9, pp. 4350-4354, Sep. 1979; Towbin et al.; Electrophoretic Transfer of Proteins from Polyacrylamide Gels to Nitrocellulos Sheets: Procedure & Some Applications.
MOCZ et al.; Analytical Biochemistry; vol. 143, pp. 283-292; 1984; Use of Cationic Detergents for Polyacrylamide Gel Electrophoresis in Multiphasic Buffer Systems.
Drager et al.; Analytical Biochemistry; vol. 145; pp. 47-56; 1985; High-Performance Anion-Exchange Chromatogrpahy of Oligonucleotides.
Analytical Biochemistry; vol. 84, pp. 622-627; 1978; Polyquarternary Amines Prevent Peptide Loss from Sequenators.

Primary Examiner—Ellis P. Robinson
Assistant Examiner—Susan S. Rucker
Attorney, Agent, or Firm—Cushman, Darby & Cushman

[57] ABSTRACT

The invention relates to a procedure for the transfer and immobilization of proteins onto a free surface formed on a chemically inert support, preferably porous glass, from a medium likely to contain them which is brought into contact with this surface. The said surface is composed of a film of a vinylpyridine polymer in which the nitrogen atom of the pyridyl moiety is substituted by an alkyl group, in particular by a methyl group; the proteins and/or the nucleic acids are brought into contact with the said surface in solution in the presence of a detergent bearing a negative charge, in particular SDS. The invention also relates more particularly to the supports coated with the said films, in particular as a monomolecular layer.

9 Claims, No Drawings

AGENTS AND PROCEDURES FOR THE TRANSFER OF PROTEINS AND/OR NUCLEIC ACIDS ONTO A SUPPORTED RECEPTOR SURFACE

The present invention is a "continuation in part" of the American patent application No. 866,250 filed on May 23, 1986 and the content of which is to be considered as constituting part of the present description (incorporated by reference).

The invention relates to agents for binding and retaining proteins and/or nucleic acids such as RNAs or DNAs on a supported surface, preferably that of a porous support, to which they are applied and this to be done by techniques involving their transfer from solutions containing them which have been applied to this surface.

For semantic convenience, the expression "proteins" is used in the description which follows to designate not only proteins according to the commonly accepted meaning of this term, including antigenic proteins, but also all other polypeptides, lipoproteins, glycoproteins, protein fragments, organic polymers or polyglycans. The invention applies more particularly to the binding and immobilization of one or more proteins on the above-mentioned supported surface after their transfer from a slab or strip of gel, for example one based on polyacrylamide.

The procedure according to the invention for transfer and immobilization of proteins onto a free surface formed on a chemically inert support, preferably porous, from a medium which is able to serve as a source of them which is brought into contact with this surface, is characterized in that the said surface from which proteins and/or nucleic acids are preferably absent initially is composed of a film of a vinylpyridine polymer, characterized by the following general formula:

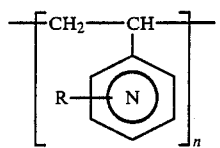

in which:

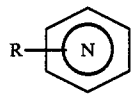

is a pyridyl moiety in which the nitrogen atom is in position 2, 3 or 4 of the ring and is substituted by an alkyl group containing 1 to 20 carbon atoms, and n is a whole number large enough so that the polymer is rendered insoluble in non polar organic solvents such as diethyl ether and ethyl acetate but not exceeding the value which would lead the polymer to become insoluble in water, and where appropriate, in dimethylformamide or methyl alcohol as well, and in that the proteins and/or nucleic acids are brought into contact with the said surface in solution in the presence of a detergent bearing a negative charge, in particular SDS, the concentration of the detergent being high enough to maintain the said proteins and/or the said nucleic acids in solution, if this is necessary, but without exceeding the concentration which would lead to a too selective binding of the detergent to the surface of the said film to the detriment of the proteins and/or of the nucleic acids.

In the preferred types of polymers R is constituted by a methyl, ethyl or pentyl group. The most preferred polymers of polyvinylpyridine are composed of salts of poly(2-vinyl-N-methylpyridine) of formula VI and salts of poly(4-vinyl-N-methylpyridine) of formula VII, both of which are shown below:

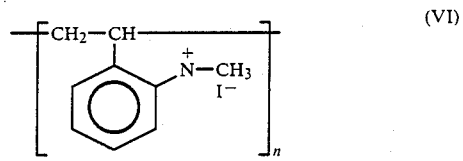 (VI)

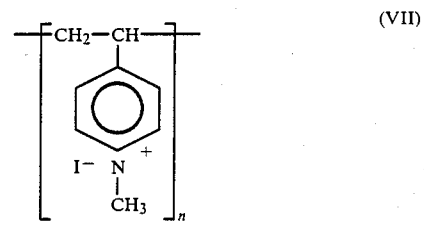 (VII)

It is important to clarify some of the concepts mentioned in the preceding definition of the procedure according to the invention. The expression "chemically inert" relates to any support capable of resisting the aqueous and organic solvents commonly used in the techniques of sequencing and of acid hydrolysis referred to above and also to the temperatures commonly used.

In particular, this support may be composed of any material, preferably porous, resistent to solutions of 6N hydrochloric acid at a temperature of 110° C. for 24 hours.

An appropriate material, answering to this condition, is constituted by glass. In a non-limiting manner, the support will be constituted of fiber glass.

Other materials can also be used as supports for carrying out the procedure of the invention. Mention will be made, as non-limiting types of examples, of polymers of methacrylic acid of formula I below:

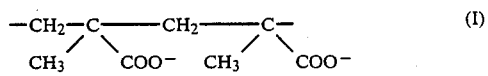 (I)

copolymers of methacrylic acid and ethylene of the formula II shown below:

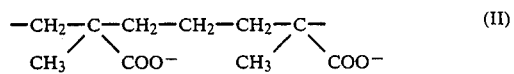 (II)

copolymers of vinyl chloride and vinylacetate of the formula III shown below:

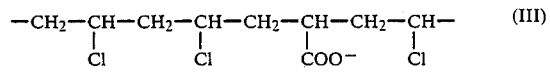 (III)

polymers of cis-oleic acid of the formula IV shown below:

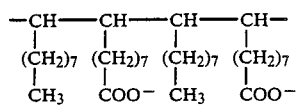

Similarly, the expression "surface of a support" does not exclude the possibility, particularly when the support is porous, that the proteins may penetrate into the interior of this support. In fact, in the event of binding, such penetration makes possible the binding and immobilization of larger quantities of protein than would be possible to a smooth surface. Nonetheless, it is clear that "macroscopically" one is still dealing with a surface, particularly when this support is available in the form of a sheet or a membrane.

The expression "the proteins are brought into contact with the said surface in solution in the presence of a detergent . . ." should not necessarily be taken literally. Here again, one is faced with an apparent phenomenon. It cannot be excluded that, on immediate contact with the free surface, a precipitation is produced of complexes between the detergent and the proteins at the very moment at which they are transferred. In particular, the intervention of such complexes in the observed immobilization of the said proteins cannot be excluded.

Similarly, the specialist is in a position to adjust the concentrations of detergents used to comply with the prevailing condition expressed in the above-mentioned general definition of the invention. These relative concentrations may depend on the nature of the detergent used. When the transfer is carried out from a gel, following fractionation of the proteins by electrophoresis, as in the preferred cases which will be mentioned later, the initial content of the detergent in the gel itself will also usually be sufficient to ensure the transfer and immobilization of these proteins to the free surface of the support.

In a variant of the invention and one invoked particularly when the detergent used is constituted by SDS, the free surface of the support includes groups which are bearers of positive charge. Advantageously, the support is composed of glass.

In one alternative implementation of the invention, the glass support is "pre-activated" with a view to producing a larger number of silanol groups present at the surface. In doing this, the capacity for binding of the polymer to the support and the amount of protein subsequently immobilized on this support will be increased. The pre-activation of the support can be carried out by addition to a solution of concentrated trifluoracetic acid at temperatures varying from about 25° C. to about 50° C. for a time varying from about 30 mn to about 8 hours. The preactivation of the fiber glass support may also be carried out by addition to a solution of concentrated nitric acid at ambient temperature for a time varying from about one to about eight hours.

The invention thus takes advantage of the capacity of the continuous film at the surface of the glass to form ionic linkages with the negatively charged silanol groups present at the surface of the porous glass and, where appropriate, to mask silanol groups not taking part in the binding reaction.

The establishment of those ionic linkages is sufficient to lead to the deposition of an at least monomolecular film of the polyvinylpyridine polymer from solutions containing it onto the surface of the glass, while preserving its capacity to absorb proteins even in the presence of a detergent bearing a negative charge, in particular in the presence of SDS.

The polyvinylpyridines may be prepared by a procedure such as that described in the publication of Kavanov V.A. Et al., Vysokomol, Soyed. A10:No. 7, 1618–1632, 1968, as well as in the publications of V. Bazhant, V. Khvalovski and I. Ratouski, Silicones, publ. by "Khimiya", 1960; N.D. Zakharov, New Typres of Rubbers and their Practical Uses, publ. by Central Bureau of Tech. Informat., Yaroslvl, 1962.

With more particular regard to the preferred poly(4-vinyl-N-methylpyridine) polymer, which may be prepared from the 4-vinyl pyridine monomer, the following procedure may be used. 4-vinyl-pyridine is block-polymerized at 45° C. by the addition of benzoyl peroxide. After four hours, the poly-4-vinyl pyridine is poured into cold diethyl ether. After the solvent has been decanted, the polymer is redissolved in t-butanol and the alcohol is re-evaporated to give a dry polymer. The polymer is redissolved in a minimal volume of dimethylformamide and it is methylated by adding a two-fold molar excess of methyl iodide.

After the polymer has been stored for four days 45° C., the polycation is precipitated by being poured into diethyl ether. The methylated polymer is recovered by filtration, dried under a vacuum and stored at 4° C. in the absence of light.

Generally speaking, recourse may be had to any detergent composed of hydrophobic chairs, in particular those of aliphatic or aromatic character, these chains bearing in addition groups sufficiently hydrophilic to make the chains soluble in water. Furthermore, these detergents must be capable of promoting the solubilization of the proteins in aqueous media.

As examples of other detergents, mention may be made of stearic acid, palmitic acid, deoxycholate. Advantageously, the medium from which the proteins are transferred to the free surface of the film is itself composed of a polyacrylamide gel containing SDS. The transfer can then be effected as a consequence of the intimate contact between the gel strip and the support bearing the above-mentioned film, the transfer being carried out in any appropriate manner (diffusion, convection, electro-elution, etc).

When recourse is had to an external buffered solvent to promote this elution, a standard buffered solution may be used. As non-limiting examples of buffered solutions mention will be made of solutions containing 50 mM of sodium borate, (pH: 8.0), transport solutions containing tris-HCl, tris-glycine to which 20% methanol may have been added.

When the polymer used is a poly(4-vinyl-pyridine) it is particularly desirable to use in the procedure according to the invention a buffer based on tris-(hydroxymethylamino) methane borate, in particular at concentrations varying from 10 mM to 200 mM, and more especially from 40 to 60 mM. Advantageously, the buffer is essentially free from sodium borate.

In an alternative form of the procedure of the invention in which a fiber glass support coated with poly(4-vinyl-N-methylpyridine) iodide is used, a preferred buffer is a solution of tris-(hydroxy-methylamino) methane borate (50 mM), in particular at pH 8.3.

In the case in which the concentration of SDS in the gel is sufficient to insure the solubilization of the proteins, it is usually not necessary to work with a buffered solution which itself contains detergents. The detergent content of the gel is usually sufficient to promote the transfer under the conditions which have been set out. This is the case in particular when the SDS content employed in the polyacrylamide gel used for first carrying out the electrophoresis of a mixture of proteins amounted to 0.1% SDS.

It is revealing that the invention takes advantage of the priori contradictory properties of the various constituents employed. Indeed, it will be recalled that the above-mentioned polymers of polyvinylpyridine are soluble in water. However, their binding to the inert support protects them from this property which otherwise could be disadvantageous, particularly if the volumes of buffered solution used to carry out the elution were relatively large. That is the reason why it is not advantageous to use a support, the surface of which is coated with unbound polyvinylpyridine polymer. When placed in contact with an appropriate solution, this latter type of support would pick up proteins which would subsequently be lost, for example, during repeated washings of the support free surface.

The presence of "unbound" polymer could also be troublesome for an additional reason. In fact, the polymer and the SDS are capable of forming complexes which are insoluble in water. Their possible formation would then be an obstacle to the complete transfer of proteins from the gel to the supported film. Finally, the binding of the polymer in the form of a fine film to the surface of the inert support does not hinder the washing of the free surface retaining the protein with organic solvent, including those which readily dissolve the polymer.

It should of course be clear, that, in the preceding technique, the polyacrylamide gel can be replaced by any other gel, for example gels based on agarose, Sephadex, cellulose, etc.

The invention also related to a particularly simple procedure for the manufacture of supported films which comply with the requirements outlined above. In particular, the procedure for the formation of a film rendered insoluble with respect to aqueous or organic solvent on a chemically inert support, preferably porous, and bearing negatively charged groups is characterized by the placing in contact of the surface of this support with an aqueous or organic solution of the above-mentioned polyvinylpyridine polymer in order to form an at least monomolecular hydrophobic film, bearing an excess of positive charges at its surface, and which is retained as an insolubilized film after rinsing and drying of the coated support. Appropriate organic solvents include methanol, ethanol, dioxane and pyridine.

Any known procedure may be used to effect the placing in contact of the support and the polybase, in particular it may be done by simply pouring the solution of polybase onto the support, by immersion of the support in a solution of the polybase used for a time varying from about 15 minutes to about 6 hours.

It is for the specialist to determine by simple routine tests the optimal duration of contact needed to obtain a satisfactory coating, in particular as a function of the products used.

In the preferred example in which fiber glass is used as support and following an alternative procedure, the glass fibers are broken by ultrasonic in order to produce glass microfibers. These microfibers are then suspended in a solution of the polybase to be used, then filtered. The microfibers coated with the insolubilized film are then passed through a press in order to produce sheets of the desired thickness.

The detection of the proteins immobilized when the procedure of the invention is used is carried out by staining the support by means of a dye. Appropriate dyes include a solution of fluorescamine in acetone, at concentrations varying from 1 mg/200 ml to 1 mg/l; iron cacodylate according to the method described by Moeremans M. et al., Anal. Biochem. 1986, 153, 18–22; 3,3'-dipentyloxacarbocyanine iodide according to the method described by Aebersold R. et al., J. Biol. Chem. 1986, 261, 4229–4238.

As an alternative, the proteins can also be detected by exposing the support to ultraviolet light. It will be obvious that the immobilized proteins can also be detected by any other known means, in particular by fluorescence.

In the foregoing, particular reference has been made to the transfer of proteins contained in a slab of gel to the free surface of a chemically inert support. It will be obvious that the medium from which the proteins are derived may be of any other kind, for example, it may consist of a sheet of nitrocellulose or porous Nylon containing proteins in the adsorbed state and which may be eluted from the support under appropriate conditions.

The procedure of the invention lends itself particularly readily to the determination of partial amino-acid sequences of proteins. The support can, in fact, be cut into slices so that only the portion containing the immobilized proteins is retained. This portion is then placed in the reaction chamber of a gas phase sequenator in order to analyze the amino acid sequence.

It will be obvious that the invention can also be applied to the determination of the total amino acid composition of various types of proteins. In this case, the portion of the support containing the immobilized proteins is treated with acid, usually 6 N HCl, or acid vapors. The amino acids are then analyzed by the standard methods.

The principle of the present invention can also be used to detect the presence of an antibody in a biological sample. In this alternative utilization, the antigenic proteins are bound to the support, then the latter is washed with a solution of proteins in order to saturate any residual binding sites on the support. Saturation is effected with a solution of non-specific proteins, possibly with a mixture of such proteins, a whole serum, or any combination of these possibilities, it being clear that the saturation solution must not interfere or react with the specific antibodies of the detection assay.

The support to which the antigenic proteins are bound is then placed in contact with a biological sample which is to be investigated for the presence of the desired antibody. After washing in order to remove the products of the reaction present in excess, the support is placed in contact with a second antibody directed against the first antibodies, this second antibody being coupled to an enzyme such as peroxidase or phosphatase. This latter may be, for example, a mouse anti-rabbit antibody in the case inw hich the first antibody which is the object of the investigation is derived from the rabbit. The presence of the desired antibody is revealed by adding a reagent which forms a colored precipitate as a result of the action of the enzyme coupled to the second antibody. As examples of suitable reagent mention will be made of 4-chloronaphthol which can be used with peroxidase and a mixture of 5-bromo-4- chloro-3-indolyl-phosphate and 2-nitro-tetrazolium which can be used with phosphatase.

The procedure of the invention can also be applied in the reverse sense where it is desired to detect the presence of antigenic proteins in a mixture of proteins by specific reaction with the complementary antibodies.

It will be obvious that the principle of the present invention can also be used to adsorb all kinds of particles present in charged detergent micelles, for example, oil droplets or lipids, onto glass or inert supports possessing the properties described above.

The procedure may also be used to purify detergents containing suspensions in a very simple manner. Once saturated, the materials absorbed can then be removed by organic solvents and the filtering support can be recharged by being passed into a solution of a polybase.

Still other characteristics of the invention will become apparent in the course of the description which follows of the conditions under which the transfer of various proteins was effected from appropriate media to a free surface mounted on an inert support meeting the criteria which had been specified earlier.

Generally speaking, the conditions described in the present application for the transfer of different proteins from a polyacrylamide gel containing SDS to fiber glass coated with Polybrene are also applicable to supports coated with polyvinylpyridine. The same can be said for:
  materials and methods,
  ways of preparing sheets of fiber glass coated with a film of vinylpyridine,
  conditions under which the proteins under study are transferred to these sheets from a polyacrylamide gel,
  acid hydrolysis and analysis, including sequencing, of the proteins under study.

EXAMPLE OF THE TRANSFER OF PROTEINS FROM POLYACRYLAMIDE GELS TO FIBER GLASS SUPPORTS COATED WITH DIFFERENT POLYBASES

In what follows a description will be given of comparison which make use of sheets of fiber glass coated with films of the substance known under the trade name of Polybrene and with poly(4-vinyl N-methylpyridine) iodide, hereinafter designated for reasons of convenience by the abbreviation P4VMP.

A—Materials

The chemical substances and the proteins used are identical with those described in Vandekerckhove J. et al., (1985) Eur. J. Biochem. 152, 9–19 and in the parent application.

Sheets of fiber glass GF/C and GF/F (commercially available from the Whatman Company) are coated separately with Polybrene and P4VMP by immersing them for 5 minutes in an aqueous solution containing 2.5 mg/ml of the polybase chosen. The sheets are then dried in air at ambient temperature and stored. Immediately before being used the sheets are washed twice in 100 ml of water in order to remove non absorbed polybase.

The drying step for the sheets coated with P4VMP is carried out in the absence of light in order to prevent secondary fluorescence phenomena from taking place.

B—Analysis on One- and Two-Dimensional Polyarylamide Gels

The proteins are separated on one-dimensional gels according to Laemmli, U.K., (1970) Nature 277, 680–781; and on two-dimensional gels according to Garrels, J.I. (1979) J. Biol. Chem. 254, 7961–7977.

Gels of 1.5 mm thickness are used in all of the experiments.

C—Transfer of Proteins

The electrotransfer of the proteins was carried out as described by Vandekerckhove (1985) already cited) and in the parent application by using transfer buffers and various polybases. The fiber glass sheets are washed rapidly (at least three times) with 100 ml of 20 mM NaCl, 10 mM sodium borate, pH = 8.0 in order to effect an ion exchange of the bound glycinate.

D—Detection of the Immobilized Proteins

The proteins are detected under ultraviolet light in the form of strongly fluorescent "spots" (mineral lamp, UVL. 56, Ultraviolet Products Inc., San Gabriel, USA). The fluorescence of the "spots" is usually sufficient to enable the large majority of the protein bands to be localized.

If this procedure fails, the proteins are visualized by dipping the fiber glass sheets into a dilute solution of fluorescamine (1 mg of fluram for 600–1000 ml HPLC grade acetone).

Other detection procedures may be used such as those described earlier: Moeremans, M. (1986), Aebersold, R. (1986).

E—Gas Phase Sequencing of the Immobilized Proteins

The protein bands are cut out from the fiber glass sheets to give bands 12 mm in length.

Up to three bands can be loaded simultaneously in the reaction chamber of a gas phase sequentor (Applied Biosystems Inc).

When the protein of interest is present in a minor band (for example in the case in which the protein is obtained in the form of a immuno-precipitate and must be separated from the polypeptides of the antibody), it is necessary to recover the bands from several of the appropriate slices of gel in order to obtain sufficient material. The fragments thus collected cannot all be placed in the reaction chamber of the sequenator. It is thus necessary to recover the gel slices and to macerate them by ultrasonication in a small volume of water. The paste obtained is then pressed onto a TEFLON filter 12 mm in diameter and the new glass filter pellet is then dried and loaded for sequencing.

The sequencing procedure is carried out without any modification to the normal programme being required. The phenylthiohydantoins of the amino acids released at each step are identified using a PTH-amino acid analyzer (120A Applied Biosystems Inc.)

F—Identification of Cysteine

The method of S-4 pyridylethylation described in Friedman, M, et al., (1970) J. Biol. Chem 245, 3868–3871 is adapted so that the reaction can be carried out in at least 50 microliters of buffer.

In addition, the protein sample (between 1 and 100 micrograms) is dissolved in 50 microliters of 0.125 M Tris-HCl, pH=9.0 containing 10% glycerol, 1 mM dithiothreitol and 0.1% SDS and reduction is allowed to proceed for two hours at 25° C. The free sulfhydryl groups are allowed to react for one hour at ambient temperature with 4-vinylpyridine after addition of 5 microliters of a 10% suspension in water. At the completion of reaction, the sample is neutralized with 0.1 N HCl until the pH indicator added turns red (pH=7.0). The neutralized sample is loaded onto the gel and hence the pH indicator serves as a colored control marker during electrophoresis.

The PTH-derivative of S-beta-4-pyridylethyl cysteine is eluted between the corresponding derivatives of eucine and isoleucine in the system for the separation of PTH-amino acids described by Hunkapiller and Hood (1983) Methods Enzymol. 91, 486–493 and appears before the phenylthiourea peak in the separation profile obtained by using a PTH-amino acid analyzer (Applied Biosystems Inc. 120A).

It was shown earlier that the proteins can be electro-eluted in a sodium borate buffer, pH=8.0 and be absorbed onto sheets of fiber glass coated with Polybrene. However, these conditions may not always be optimal for all proteins. The optimal conditions for elution are usually conditions permitting a low degree of binding and vice-versa. Extreme limits may be defined:

the addition of 0.05% SDS to the transfer buffer always leads to complete elution but does not permit binding, whereas the addition of methanol (35%) to the transfer buffer leads to the retention of most of the proteins in the gel but those which are eluted are immobilized in very high yield.

These contradictory effects may be explained as follows: In view of the fact that the transfer takes place in the absence of SDS from the transfer buffer, the only SDS present is to be found in the gel of 1.5 mm thickness. Thus, during their electromigration, the proteins are surrounded by a continually decreasing concentration of free SDS molecule and of SDS micelles resulting in the continuous release of bound SDS and the continuous formation of new complexes containing less bound SDS. This effect may be influenced by:

the type and concentration of the transfer buffer,
impurities in the SDS, in particular C16 alkyl sulfates,
the presence of organic solvents (such as methanol).

This results in the SDS-protein complexes migrating more slowly and some of them may even become insoluble.

The binding of the proteins is probably due to a Coulombic attraction being established initially between the dodecylsulfate and the positively charged quaternary ammonium groups, the binding continually increasing owing to hydrophobic interactions between the side chain of the detergent, the polybase and the proteins.

In the experiments described in the discussion which follows various buffer systems for electro-transfer possessing a less marked degrading activity of the SDS have been combined with different polybases possessing a higher charge density. Polybrene, one of the polybases used, contains quaternary ammonium ions alternating with trimethylene and hexamethylene hydrophobic bridges. Other potentially interesting polybases used contain a higher charge density balanced by groups possessing a sufficiently hydrophobic character.

Among the different polybases studied, poly-(4-vinyl-N-methyl-pyridine) iodide (P4VMP) has shown the most interesting binding capacities. The different results obtained with the supports coated with POLYBRENE as opposed to the results obtained with supports coated with P4VMP have been particularly clearly demonstrated in the case in which tris-borate is used as elution buffer.

POLYBRENE showed a considerable decrease in its capacity for binding whereas P4VMP maintained its original capacity for binding. Table II below presents an evaluation of the different transfer systems tested with the following proteins: actin, bovine serum albumin, carbonic anhydrase, chymotrypsinogen, human hepatitis B antigen, human gamma interferon, myoglobin, ovalbumin, phosphorylase B, tissue activator of human plasminogen and tublin.

Examination of Table II below shows that the best conditions of fixation are obtained as follows:

the gels containing more than 12.5% of acrylamide are fixed better with methanol (20%). The fixation is then carried out in a tris-borate buffer (+20% methanol) on glass coated with P4VMP or in sodium borate buffer (+20% methanol) on glass coated with Polybrene.

the gels containing lower percentages of acrylamide are fixed better with tris-borate buffers on sheets coated with P4VMP.

These conditions make it possible to immobilize about 20 to 25 micrograms of protein per $cm^2$ on sheets of fiber glass (Whatman GF/C). In the case where a thicker paper (Whatman GF/F) is used, the capacity is proportionately greater (from 1.5 to 2 times). Thus, binding capacities obtaining 50 micrograms per $cm^2$ for actin and human serum albumin have been obtained.

TABLE II

| Transfer buffer | POLYBRENE | P4VMP | Elution time |
|---|---|---|---|
| 50 mM sodium borate pH 8,0 | ++ | ++ | 20 hours |
| 50 mM sodium borate pH 8,0, methanol 20% | ++++ | +++ | 24 hours |
| 50 mM Tris-borate pH 8,5 | + | ++++ | 7 hours |
| 50 mM Tris-borate pH 8,5, methanol 20% | +++ | ++++ | 10 hours |

The efficacies of transfer and binding are given in a semi-quantitative manner and are measured on fiber glass (Whatman GF/C) coated either with Polybrene or with P4VMP.

The conditions under which it is possible to recover more than 60% of all of the proteins are represented by (+++++), 60% of most of the proteins by (++++) (+++) represents a recovery of between 40% and 60% of most of the proteins, a high capacity of fixation associated with a low power of elution is represented by (++), a low recovery and irreproducible results are represented by (+).

The electrotransfer is carried out at 5 V/cm.

The transfer procedure according to the invention thus furnishes means to carry out a particularly efficacious and reproducible "in situ" sequencing starting from extremely minute quantities of proteins.

I claim:

1. A coated support for use in the transfer and immobilization of proteins or nucleic acids, or mixtures thereof, which coated support comprises:
   (i) a chemically inert support capable of resisting the aqueous and organic solvents commonly used in the techniques of sequencing and of acid hydrolysis, and (ii) at least a monomolecular film of a vinylpyridine polymer, said vinyl pyridine polymer being immobilized and insolubilized with respect to said aqueous or organic solvents on a surface of said chemically inert support, wherein said vinyl pyridine polymer has the general formula:

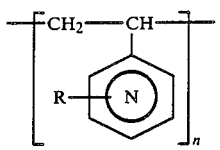

in which:

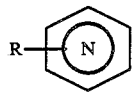

is a pyridyl moiety in which the nitrogen atom is in position 2, 3 or 4 of the ring and is substituted by an alkyl group containing 1 to 20 carbon atoms, and n is a whole number large enough so that the vinylpyridine polymer is rendered insoluble in non polar organic solvents but not exceeding the value which would lead the vinylpyridine polymer to become insoluble in water.

2. The coated support according to claim 1, wherein said chemically inert support is selected from the group consisting of glass, polymers of methyl acrylic acid, copolymers of methylacrylic acid and ethylene, copolymers of vinyl chloride and vinyl acetate, and polymers of cis-oleic acid.

3. The coated support according to claim 2, wherein said chemically inert support is porous glass.

4. The coated support according to claim 3, wherein the vinylpyridine polymer is poly(2-vinyl-N-methylpyridine), poly(4-vinyl-N-methylpyridine), or a salt thereof.

5. The coated support according to claim 1, wherein the vinylpyridine polymer is soluble in dimethylformamide.

6. The coated support according to claim 1, wherein the vinylpyridine polymer is soluble in methylalcohol.

7. The coated support according to claim 1, wherein the vinylpyridine polymer is insoluble in diethyl ether 8. The coated support according to claim 1, wherein the vinylpyridine polymer is insoluble in ether acetate.

9. The coated support according to claim 1 wherein said chemically inert support and said film are comprised of different materials.

* * * * *